United States Patent [19]

Horton

[11] 4,309,898
[45] Jan. 12, 1982

[54] SIGNAL-TO-NOISE RATIO IN CHROMATOGRAPHIC ANALYSIS

[75] Inventor: Robert L. Horton, Bartlesville, Okla.

[73] Assignee: Phillips Petroleum Co., Bartlesville, Okla.

[21] Appl. No.: 161,179

[22] Filed: Jun. 19, 1980

[51] Int. Cl.[3] ............................................. G01N 31/08
[52] U.S. Cl. ...................................................... 73/23.1
[58] Field of Search ........................... 73/23.1, 61.1 C; 422/89

[56] References Cited

U.S. PATENT DOCUMENTS

| | | | |
|---|---|---|---|
| 3,357,233 | 12/1967 | Roof | 73/23.1 |
| 3,538,744 | 11/1970 | Karasek | 73/23.1 |
| 4,150,561 | 4/1979 | Zupanick | 73/23 |
| 4,185,490 | 1/1980 | Clouser et al. | 73/23.1 |

OTHER PUBLICATIONS

M. H. Aronson, Lock-In and Carrier Amplifiers, Measurements and Data Corporation, pp. 1-15, 1978.

Primary Examiner—Stephen A. Kreitman

[57] ABSTRACT

In a chromatographic analysis system, carrier fluid containing a sample fluid and pure carrier fluid are alternately supplied to both first and second fluid inlets of a chromatographic detector. Lock-in detection of the output of the chromatographic detector based on the frequency at which the carrier fluid containing a sample fluid and pure carrier fluid are alternately provided to both of the fluid inlets of the chromatographic detector provides a significant signal-to-noise improvement in the chromatograph.

19 Claims, 4 Drawing Figures

SIGNAL-TO-NOISE RATIO IN CHROMATOGRAPHIC ANALYSIS

This invention relates to chromatography. In one aspect, this invention relates to method and apparatus for enhancing the signal-to-noise ratio in chromatography.

A chromatographic analyzer is an analytical instrument that is used to separate in time and individually detect the constituents of a sample to be analyzed. The chromatographic analyzer typically includes an analytical column through which a carrier fluid is passed continuously. The sample to be analyzed is injected into the carrier stream and is thus carried through the analytical column. The sample constituents are carried through the analytical column at different velocities and in this manner the sample constituents are separated in time.

A detector is employed to detect the separated constituents and the detector output signal typically is plotted as a function of time to produce what is termed a chromatogram. As each sample component is eluted from the column, the component produces a sharp increase in the detector output signal amplitude, which increase appears as a spike or peak in the chromatogram.

If a constituent having a very low concentration is eluted from the analytical column, the signal-to-noise ratio of the detector response may be one or even less than one. If this situation occurs, the information concerning the concentration of the minor sample component may be lost. Amplification of the detector response will not provide any improvement because the noise will also be amplified. Even if the sample component has a high concentration and the signal-to-noise ratio is greater than one it is desirable to improve the signal-to-noise ratio to provide a more accurate chromatogram.

It is thus an object of this invention to provide method and apparatus for enhancing the signal-to-noise ratio in chromatography.

In accordance with the present invention, method and apparatus is provided whereby carrier fluid containing a sample fluid and pure carrier fluid are alternately supplied to both of the fluid inlets of a chromatographic detector. Lock-in detection of the output of the chromatographic detector based on the frequency at which the carrier fluid containing a sample fluid and pure carrier fluid are alternately provided to both of the fluid inlets of the chromatographic detector provides a significant signal-to-noise improvement in the chromatogram.

Other objects and advantages of the invention will be apparent from the foregoing brief description of the invention and the claims as well as from the detailed description of the invention in which:

Figure 1:
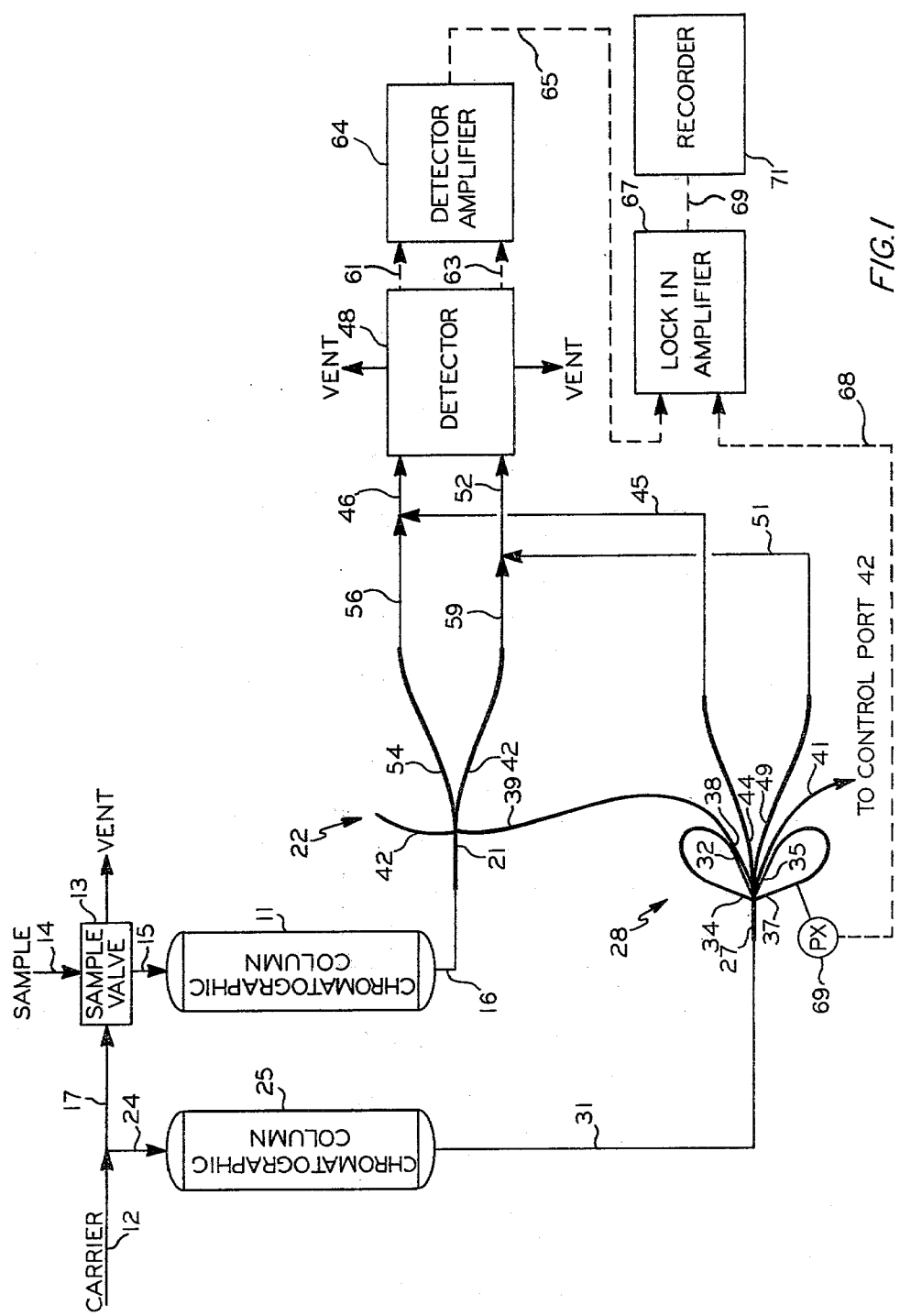
FIG. 1 is a diagrammatic illustration of a first embodiment of a chromatographic analyzer system employing fluidic bistable flipflops and lock-in detection.
Figure 3:
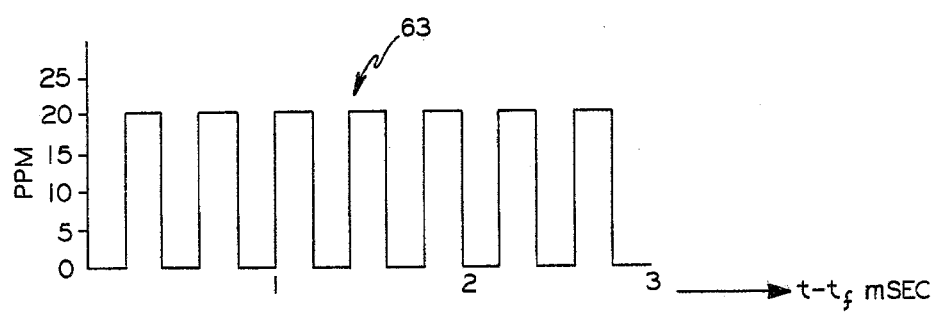
Figure 3:
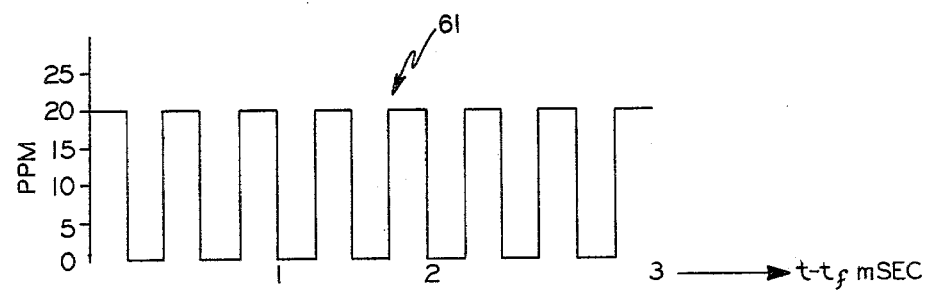
Figure 4:
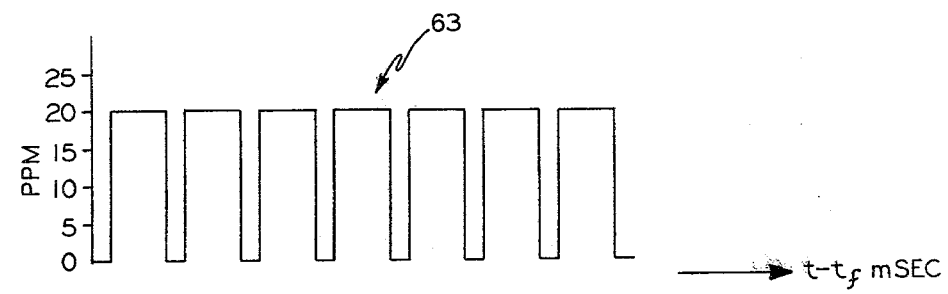
Figure 4:
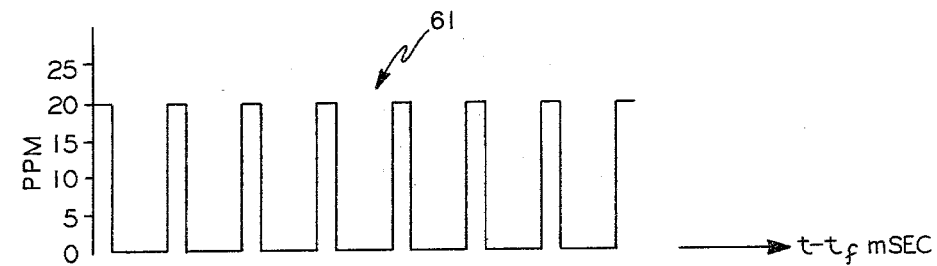

FIG. 3 is an illustration of the output waveforms from the chromatographic detector in the chromatographic analyzer system of FIG. 1 when all the feedback loops associated with the fluidic bistable flipflops are the same length; and FIG. 4 is an illustration of the output waveforms from the chromatographic detector in the chromatographic analyzer system of FIG. 1 when all the feedback loops associated with the fluidic bistable flipflops are not the same length.

The invention is described in terms of a specific chromatographic analyzer system. However, the invention is applicable to other chromatographic analyzer systems and configurations. The invention is applicable to either gas or liquid chromatography. The invention is also described in terms of using fluidic bistable flipflops to alternately supply carrier fluid containing a sample fluid and pure carrier fluid to both the sample and reference inlets of a chromatographic analyzer detectors. Other fluidic devices and techniques to provide the desired alteration could be utilized if desired.

Referring now to the drawings and in particular to FIG. 1, there is illustrated a chromatographic column 11. A sample of a fluid to be analyzed is delivered to the sample valve 13 through conduit means 14. Conduit means 15 extends between the sample valve 13 and the fluid inlet of the chromatographic column 11. Carrier fluid is provided through the combination of conduit means 12 and 17 to the sample valve 13. Carrier fluid flows through sample valve 13 and chromatographic column 11 to the supply port 21 of the fluidic amplifier 22 which is a bistable flipflop. At the beginning of an analysis period, sample valve 13 is actuated to introduce a predetermined volume of sample into the carrier fluid flowing through chromatographic column 11. The constituents of the sample are eluted in sequence and flow from the chromatographic column 11 through conduit means 16 to the supply port 21 of the fluidic bistable flipflop 22.

Carrier fluid is provided through the combination of conduit 12 and 24 to the fluid inlet of the chromatographic column 25. Any suitable flow restriction could be utilized in place of the chromatographic column 25. The chromatographic column 25 is utilized to ensure that the flow rate of the fluid flowing to the supply port 27 of the fluidic bistable flipflop 28 is equal to the flow rate of the fluid flowing to the supply port 21 of the fluidic bistable flipflop 22. The fluid outlet of the chromatographic column 25 is connected to the supply port 27 of the fluidic bistable flipflop 28 through conduit means 31.

The vent 32 of the fluidic bistable flipflop 28 is in fluid communication with the control port 34 of the fluidic bistable flipflop 28. In like manner, the vent 35 of the fluidic bistable flipflop 28 is in fluid communication with the control 37 of the fluidic bistable flipflop 28. The vent 38 of the fluidic bistable flipflop 28 is in fluid communication with the control port 39 of the fluidic bistable flipflop 22. In like manner, the vent 41 of the fluidic bistable flipflop 28 is in fluid communication with the control port 42 of the fluidic bistable flipflop 22.

Fluid flowing from the output port 44 of the fluidic bistable flipflop 28 is provided through the combination of conduit means 45 and 46 to a first fluid inlet (referred to hereinafter as the "sample inlet") of the detector 48. Fluid flowing from the output port 49 of the fluidic bistable flipflop 28 is provided through the combination of conduit means 51 and 52 to a second fluid inlet (referred to hereinafter as the "reference inlet") of the detector 48. Fluid flowing from the output port 54 of the fluidic bistable flipflop 22 is provided through the combination of conduit means 56 and 46 to the sample inlet of the detector 48. Fluid flowing from the output port 58 of the fluidic bistable flipflop 22 is provided through the combination of conduit means 59 and 52 to the reference inlet of the detector 48.

Fluidic bistable flipflops are well known in the art of fluidics. The operation and design of a fluidic bistable flipflop is described beginning at page 310 in the *Encyclopedia of Instrumentation and Control*, edited by Douglas M. Considine, McGraw-Hill Book Company, 1971. Essentially, a fluidic bistable flipflop provides alternate flow between the two output ports. Referring specifically to the fluidic bistable flipflop 28 illustrated in FIG. 1, assume that a fluid flow is provided to the supply port 27 and that the fluid flows through the output port 44. Upon entering the fluidic bistable flipflop 28, the fluid will also flow through the vent 32 and thus to the control port 34. The fluid will continue to flow through the output port 44 for the time required for the fluid to flow from the vent 32 to the control port 34. When the fluid reaches the control port 34, the fluid flow will be switched to the output port 49. Fluid will also flow from the vent 35 to the control port 37. When fluid reaches the control port 37, the fluid flow will be switched back to the output port 44. This operation continues as long as fluid is provided to the supply port 27. The frequency of the switching action is determined by the lengths of the fluid path from the point where fluid enters a vent to the point where fluid rejoins the main flow from a control port. For the sake of convenience, the fluid path from the point that fluid enters a vent to the point that fluid rejoins the main flow from a control port will be referred to hereinafter as a "feedback loop" associated with a particular control port.

In the present invention, all feedback loops associated with the fluidic bistable flipflops are preferably of equal length to provide maximum enhancement of the signal to noise ratio. However, this is not required as will be discussed hereinafter.

In the preferred embodiment, where the feedback loop associated with the control port 34 and the feedback loop associated with the control port 37 are of equal length, the flow of fluid will alternate between the output port 44 and the output port 49 at a frequency F which is adjustable by adjusting the lengths of the feedback loops. Because the frequency F is set by the reference stream which is pure carrier fluid, the frequency F will not drift with time except over the long term. Because the vent 38 of the fluidic bistable flipflop 28 is in fluid communication with the control port 39 of the fluidic bistable flipflop 22 and the vent 41 of the fluidic bistable flipflop 28 is in fluid communication with the control port 42 of the fluidic bistable flipflop 22, the flow of fluid through the output ports 54 and 58 of the fluidic bistable flipflop 22 will also alternate at the frequency F. Thus, carrier fluid containing the sample will be provided to both the sample inlet and the reference inlet of the detector 48 at a frequency F and in like manner pure carrier fluid will be provided to the sample inlet and reference inlet of the detector 48 at a frequency F.

The detector 48 may be any suitable chromatographic detector. Suitable detectors include thermal conductivity, flame ionization, ultraviolet absorption, and dielectric constant detectors. The sample side of the detector 48 provides an output signal 61 which is responsive to the concentration of a particular constituent of the sample which is flowing through the sample side of the detector 48. In like manner, the reference side of the detector 48 provides an output signal 63 which is responsive to the concentration of the same component of the sample. Preferably, the two detectors are closely matched, so that the same sample concentration in either would evoke quite similar responses. Signal 61 and 63 are provided as inputs to the detector amplifier 64, which is typically a differential amplifier. The output signal 65 from the detector amplifier 64 is responsive to the difference between signal 61 and 63.

The detector 48 and the detector amplifier 64 have been illustrated separately for the sake of illustration. The detector 48 and the detector amplifier 64 are commonly considered as a single unit with the output signal 65 being considered the output of the chromatographic detector responsive to the flow of fluid through both the sample and reference sides of the detector 48.

Signal 65, which will have a frequency F, is provided as an input to the lock-in amplifier 67. The lock-in amplifier 67 is also provided with a reference signal 68 which has a frequency F. The reference signal 68 is established by the pressure transducer 69 which is in fluid communication with the feedback loop associated with the control 37 of the fluidic bistable flipflop 28. Signal 68 could be established by other techniques such as using a flow transducer if desired.

The lock-in amplifier 67 may be considered as an operational amplifier having a negative input grounded. Signal 65 is supplied to the positive input. The feedback loop of the operational amplifier is tuned to the frequency F and this tuning is assured by the reference signal 68. The lock-in amplifier 67 presents a high impedance at the frequency F but a low impedance at all other frequencies. Thus, only the component of signal 65 at the frequency F will be amplified which provides a greatly enhanced signal-to-noise ratio. The output of the operational amplifier portion of the lock-in amplifier will be a sine wave having a frequency F. The amplitude of the sine wave may be as much as 6 to 10,000 times as great as the amplitude of the component of signal 65 which has a frequency F. The output sine wave will typically be provided to a device such as an ammeter which gives a constant DC output proportional to the amplitude of the sine wave. The constant DC output is provided as signal 69 to the recorder 71.

Fluid propagates through a fluidic device at approximately the speed of sound. The length of the feedback loops associated with the fluidic devices can thus be adjusted to give a desired frequency F. For example, the velocity of sound in hexane is about $1.3 \times 10^5$ centimeters/second. Thus, if hexane is being utilized as a carrier fluid, a feedback loop length of 13 centimeters will give a frequency F of about 10 KHz.

For the sake of illustrating the present invention, assume that pure hexane is flowing through conduit means 31 and hexane containing 20 parts per million pyrene is flowing through conduit means 16. Further assume that all of the feedback loops associated with the fluidic bistable flipflops 22 and 28 have a length of 13 centimeters such that the frequency F is 10 KHz. FIG. 3 illustrates signals 61 and 63 as a function of time. The horizontal axis on the plots illustrated in FIG. 3 is not time but $T - T_F$ where $T_F$ is the length of time required for the hexane to flow from the entrance of a fluidic bistable flipflop to the detector 48. The fluid paths are such that the time $T_F$ is equal for both fluid flowing through the fluidic bistable flipflop 22 and fluid flowing through the fluidic bistable flipflop 28. Signals 61 and 63 will be square waves having a frequency of 10 KHz.

The peak amplitude of the square waves will be representative of 20 parts per million pyrene.

The output signal 65 from the detector amplifier 64 will be a square wave having the same frequency as signals 61 and 63 but having twice the amplitude since signal 65 is responsive to the difference between signals 61 and 63. Signal 65 will be lock-in detected at a frequency of 10 KHz which will enable recovery of signals 61 and 63 even if these signals are completely buried in noise.

As has been previously stated, preferably all feedback loops are of equal length. However, this is not required. FIG. 4 illustrates operation of the present invention when the feedback loops are not all of the same length. Again assuming that hexane is the carrier fluid and pyrene is the component of the sample being eluted, the output wave forms illustrated in FIG. 4 are illustrative of the output wave forms which would be obtained where the feedback loop associated with the control port 34 and the feedback loop associated with the control port 39 have lengths of 19.5 centimeters with the remaining two feedback loops having lengths of 6.5 centimeters. A lock-in detector system would not be able to achieve as great a signal-to-noise ratio enhancement as with the preferred mode of operation but the signal-to-noise ratio would be enhanced even if all the feedback loops are not of equal length.

Figure 2:
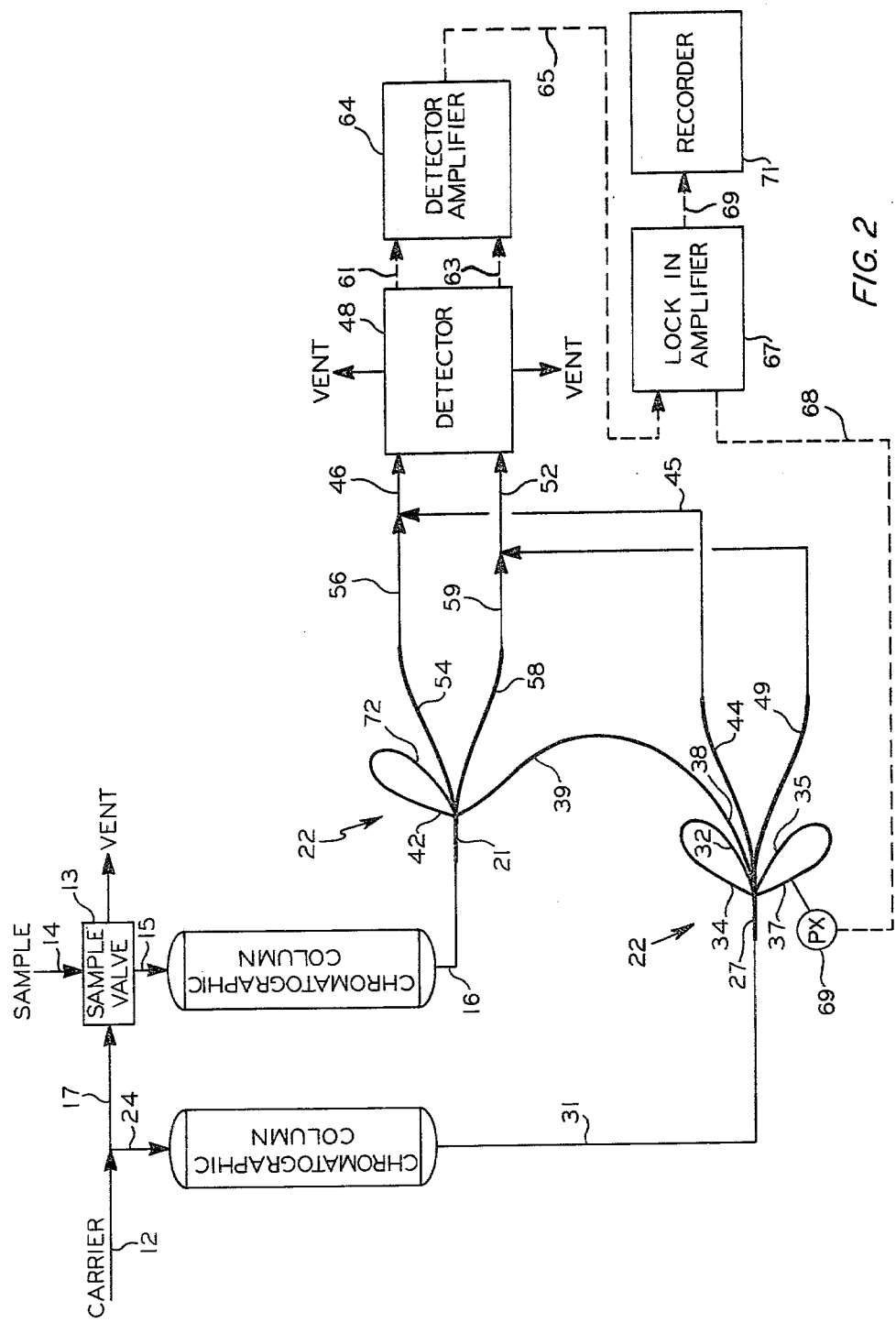
FIG. 2 is a diagrammatic illustration of a second embodiment of a chromatographic analyzer system employing fluidic bistable flipflops and lock-in detection.

FIG. 2 illustrates a less preferred mode of interconnecting the two fluidic bistable flipflops 22 and 28. The operation of the chromatographic analyzer system and the lock-in detection system is identical to that illustrated in FIG. 1. However, the coupling between the two fluidic bistable flipflops 22 and 28 has been weakened by connecting only the vent 38 to the control port 39. The control port 42 is in fluid communication with the vent 72 which is associated with the output port 54 rather than with the vent 41 as illustrated in FIG. 1. The vent 41 has been removed. The configuration illustrated in FIG. 2 may be easier to manufacture because of only the one link between the two fluidic bistable flipflops. However, operation of the system would tend to correspond more closely to that illustrated in FIG. 4 than that illustrated in FIG. 3 unless all the feedback loops are of the precisely same length.

Many other configurations of the fluidic devices are possible. FIG. 1 illustrates the preferred configuration while FIG. 2 illustrates a variation. The present invention is not limited to the configurations illustrated in FIGS. 1 and 2 but is rather applicable to any configuration of two fluidic devices which accomplishes the purpose of the present invention.

The invention has been described in terms of a preferred embodiment as illustrated in FIG. 1 and an alternative embodiment as illustrated in FIG. 2. It is reiterated that many different chromatographic analyzer configurations could be utilized and many different fluidic device configurations could be used if desired so long as a modulation of the output signal from the detector amplifier is provided in such a manner that lock-in detection may be utilized to improve the signal-to-noise ratio. While the invention has been described in terms of the presently preferred embodiment and one variation, other reasonable variations and modifications are possible by those skilled in the art within the scope of the described invention and the appended claims.

That which is claimed is:

1. Apparatus comprising:
a first chromatographic separating column having a fluid inlet and a fluid outlet;
means for supplying carrier fluid to the fluid inlet of said first chromatographic separating column;
means for injecting a sample into the carrier fluid flowing to the fluid inlet of said first chromatographic separating column;
a flow restriction means having a fluid inlet and a fluid outlet;
means for supplying carrier fluid to the fluid inlet of said flow restriction means;
a detector means capable of measuring a property of a fluid which is characteristic of the fluid, said detector means having first and second fluid inlets;
means for supplying fluid from the fluid outlet of said first chromatographic separating column and the fluid outlet of said flow restriction means alternately to both said first fluid inlet and said second fluid inlet of said detector means in such a manner that said detector means establishes a first signal, having a frequency F, representative of the response of said detector means when fluid from the fluid outlet of said first chromatographic separating column and fluid from the fluid outlet of said flow restriction means are provided to said detector means; and
means for amplifying said first signal at said frequency F to improve the signal-to-noise ratio of the response of said detector means.

2. Apparatus in accordance with claim 1 wherein said means for injecting a sample into the carrier fluid flowing to the fluid inlet of said first chromatographic separating column means comprises a sample valve.

3. Apparatus in accordance with claim 1 wherein said flow restriction means comprises a second chromatographic separating column.

4. Apparatus in accordance with claim 1 wherein said means for supplying fluid from the fluid outlet of said first chromatographic separating column and the fluid outlet of said flow restriction means alternately to both said first fluid inlet and said second fluid inlet of said detector means comprises first and second fluidic bistable flipflops.

5. Apparatus in accordance with claim 1 wherein said means for amplifying said first signal comprises a lock-in amplifier tuned to said frequency F.

6. Apparatus comprising:
a first chromatographic separating column having a fluid inlet and a fluid outlet;
means for supplying carrier fluid to the fluid inlet of said first chromatographic separating column;
means for injecting a sample into the carrier fluid flowing to the fluid inlet of said first chromatographic separating column;
a flow restriction means having a fluid inlet and a fluid outlet;
means for supplying carrier fluid to the fluid inlet of said flow restriction means;
a first fluidic bistable flipflop having a supply port, first and second output ports, a first control port associated with said first output port, a second control port associated with said second output port, first and second vents associated with said first output port, and third and fourth vents associated with said second output port;
a second fluidic bistable flipflop having a supply port, first and second output ports, a first control port associated with said first output port, and a second control port associated with said second output port, wherein the first vent of said first fluidic bistable flipflop is in fluid communication with the first control port of said first fluidic bistable flipflop thereby forming a first feedback loop, the second vent of said first fluidic bistable flipflop is in fluid communication with the second control port of said second fluidic bistable flipflop thereby forming a second feedback loop, the third vent of said first fluidic bistable flipflop is in fluid communication with the second control port of said first fluidic bistable flipflop thereby forming a third feedback loop, and the fourth vent of said first fluidic bistable flipflop is in fluid communication with the first control port of said second fluidic bistable flipflop thereby forming a fourth feedback loop;

means for supplying a fluid stream from the fluid outlet of said flow restriction means to the supply port of said first fluidic bistable flipflop;

means for supplying a fluid stream from the fluid outlet of said first chromatographic separating column to the supply port of said second fluidic bistable flipflop;

a detector means capable of measuring a property of a fluid which is characteristic of the fluid;

means for supplying fluid from the first output port of said first fluidic bistable flipflop and fluid from the first output port of said second fluidic bistable flipflop to said detector means as a first fluid stream;

means for supplying fluid from the second output port of said first fluidic bistable flipflop and fluid from the second output port of said second fluidic bistable flipflop to said detector means as a second fluid stream, said detector means establishing a first signal representative of the response of said detector means when said first fluid stream and said second fluid stream are provided to said detector means;

means for establishing a second signal having a frequency equal to the frequency at which fluid flow is being switched between the first output port and the second output port of said first fluidic bistable flipflop;

a lock-in amplifier means having a signal input and a reference input;

means for supplying said first signal to the signal input of said lock-in amplifier means; and means for supplying said second signal to the reference input of said lock-in amplifier means, said lock-in amplifier means establishing a third signal representative of the response of said detector means, wherein said third signal has a higher signal-to-noise ratio than said first signal.

7. Apparatus in accordance with claim 6 wherein said means for injecting a sample into the carrier fluid flowing to the fluid inlet of first chromatographic separating column means comprises a sample valve.

8. Apparatus in accordance with claim 7 wherein said flow restriction means comprises a second chromatographic separating column.

9. Apparatus in accordance with claim 6 wherein said first, second, third and fourth feedback loops have equal lengths.

10. Apparatus in accordance with claim 6 wherein said first and second feedback loops have equal lengths and said third and fourth feedback loops have equal lengths different from the length of said first and second feedback loops.

11. Apparatus in accordance with claim 6 wherein said means for establishing said second signal comprises a pressure transducer in fluid communication with said third feedback loop.

12. Apparatus comprising:

a first chromatographic separating column having a fluid inlet and a fluid outlet;

means for supplying carrier fluid to the fluid inlet of said first chromatographic separating column;

means for injecting a sample into the carrier fluid flowing to the fluid inlet of said first chromatographic separating column;

a flow restriction means having a fluid inlet and a fluid outlet;

means for supplying carrier fluid to the fluid inlet of said flow restriction means;

a first fluidic bistable flipflop having a supply port, first and second output ports, a first control port associated with said first output port, a second control port associated with said second output port, first and second vents associated with said first output port, and a third vent associated with said second output port;

a second fluidic bistable flipflop having a supply port, first and second output ports, a first control port associated with said first output port, a second control port associated with said second output port, and a first vent associated with said first output port, wherein the first vent of said first fluidic bistable flipflop is in fluid communication with the first control port of said first fluidic bistable flipflop thereby forming a first feedback loop, the second vent of said first fluidic bistable flipflop is in fluid communication with the second control port of said second fluidic bistable flipflop thereby forming a second feedback loop, the third vent of said first fluidic bistable flipflop is in fluid communication with the second control port of said first fluidic bistable flipflop thereby forming a third feedback loop, and the first vent of said second fluidic bistable flipflop is in fluid communication with the first control port of said second fluid bistable flipflop thereby forming a fourth feedback loop;

means for supplying a fluid stream from the fluid outlet of said flow restriction means to the supply port of said first fluidic bistable flipflop;

means for supplying a fluid stream from the fluid outlet of said first chromatographic separating column to the supply port of said second fluidic bistable flipflop;

a detector means capable of measuring a property of a fluid which is characteristic of the fluid;

means for supplying fluid from the first output port of said first fluidic bistable flipflop and fluid from the first output port of said second fluidic bistable flipflop to said detector means as a first fluid stream;

means for supplying fluid from the second output port of said first fluidic bistable flipflop and fluid from the second output port of said second fluidic bistable flipflop to said detector means as a second fluid stream, said detector means establishing a first signal representative of the response of said detector means when said first fluid stream and said second fluid stream are provided to said detector means;

means for establishing a second signal having a frequency equal to the frequency at which fluid flow is being switched between the first output port and the second output port of said first fluidic bistable flipflop;

a lock-in amplifier means having a signal input and a reference input;

means for supplying said first signal to the signal input of said lock-in amplifier means; and means for supplying said second signal to the reference input of said lock-in amplifier means, said lock-in amplifier means establishing a third signal representative of the response of said detector means, wherein said third signal has a higher signal-to-noise ratio than said first signal.

13. Apparatus in accordance with claim 12 wherein said means for injecting a sample into the carrier fluid flowing to the fluid inlet of first chromatographic separating column means comprises a sample valve.

14. Apparatus in accordance with claim 12 wherein said flow restriction means comprises a second chromatographic separating column.

15. Apparatus in accordance with claim 12 wherein said first, second, third and fourth feedback loops have equal lengths.

16. Apparatus in accordance with claim 12 wherein said means for establishing said second signal comprises a pressure transducer in fluid communication with said third feedback loop.

17. A method for improving the signal to noise ratio of the response of a chromatographic analyzer detector comprising the steps of:

providing a carrier fluid and a carrier fluid containing a sample alternately to both first and second fluid inlets of said chromatographic analyzer detector at a frequency F; and amplifying the response of said chromatographic analyzer detector, when said carrier fluid and said carrier fluid containing sample are provided alternately to both said first and said second fluid inlets of said chromatographic analyzer detector, at said frequency F to thereby improve the signal to noise ratio of the response of said chromatographic analyzer detector.

18. A method in accordance with claim 17 wherein said carrier fluid and said carrier fluid containing a sample are provided alternately to said first and second fluid inlets of said chromatographic analyzer detector in such a manner that when said carrier fluid is flowing to said first fluid inlet, said carrier fluid containing a sample is flowing to said second fluid inlet and when carrier fluid is flowing to said second fluid inlet, said carrier fluid containing a sample is flowing to said first fluid inlet.

19. A method in accordance with claim 17 wherein said step of amplifying the response of said chromatographic analyzer detector at said frequency F comprises lock in amplifying the response of said chromatographic analyzer detector.

* * * * *